(12) United States Patent
Czupi et al.

(10) Patent No.: US 10,788,964 B1
(45) Date of Patent: Sep. 29, 2020

(54) METHOD AND SYSTEM FOR PRESENTING FUNCTION DATA ASSOCIATED WITH A USER INPUT DEVICE AT A MAIN DISPLAY IN RESPONSE TO A PRESENCE SIGNAL PROVIDED VIA THE USER INPUT DEVICE

(71) Applicant: GE Precision Healthcare LLC, Wauwatosa, WI (US)

(72) Inventors: Bálint Czupi, Seewalchen (AT); Lucienne van der Veen, Geinberg (AT); Christian Perrey, Mondsee (AT); Daniel Buckton, Salzburg (AT)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/409,533

(22) Filed: May 10, 2019

(51) Int. Cl.
| | |
|---|---|
| *G06F 3/0484* | (2013.01) |
| *G06F 3/0354* | (2013.01) |
| *A61B 8/00* | (2006.01) |
| *G06F 3/044* | (2006.01) |
| *G06F 1/3231* | (2019.01) |
| *A61B 34/00* | (2016.01) |

(52) U.S. Cl.
CPC .......... *G06F 3/04842* (2013.01); *A61B 8/465* (2013.01); *A61B 8/467* (2013.01); *A61B 34/25* (2016.02); *G06F 1/3231* (2013.01); *G06F 3/0354* (2013.01); *G06F 3/044* (2013.01); *G06F 2203/04101* (2013.01)

(58) Field of Classification Search
CPC ......... G06F 1/3231; G06F 2203/04101; G06F 2203/04108; G06F 3/04842; G06F 3/044; G06F 3/0416; G06F 3/017; G06F 3/0412; G06F 1/1626
See application file for complete search history.

(56) References Cited

U.S. PATENT DOCUMENTS

| | | | |
|---|---|---|---|
| 5,341,133 A | 8/1994 | Savoy et al. | |
| 10,318,034 B1 * | 6/2019 | Hauenstein | ......... G06F 3/04842 |
| 2003/0025676 A1 * | 2/2003 | Cappendijk | ......... G06F 3/04886 |
| | | | 345/173 |
| 2006/0232557 A1 | 10/2006 | Fallot-Burghardt | |
| 2012/0254808 A1 * | 10/2012 | Gildfind | .............. G06F 3/04812 |
| | | | 715/863 |
| 2014/0121524 A1 * | 5/2014 | Chiang | .................. G16H 30/20 |
| | | | 600/459 |

(Continued)

*Primary Examiner* — Sanjiv D. Patel
(74) *Attorney, Agent, or Firm* — McAndrews, Held & Malloy, Ltd.; Jacob Groethe; David Bates

(57) ABSTRACT

A system and method for presenting function data associated with a user input device at a main display in response to a presence signal provided via the user input device is provided. The method includes receiving, at a processor of an ultrasound system, a presence signal from a presence sensor of a user input device of the ultrasound system. The presence signal is provided by the presence sensor in response to a detection of a user at a proximity to the user input device. The presence signal is independent from an actuation signal provided by the user input device in response to user actuation of the user input device. The method includes processing, by the processor, the presence signal to present function data identifying a functionality of the user input device at a main display of the ultrasound system.

20 Claims, 7 Drawing Sheets

(56) References Cited

U.S. PATENT DOCUMENTS

| | | | |
|---|---|---|---|
| 2015/0062033 A1* | 3/2015 | Ishihara | G06F 3/017 |
| | | | 345/173 |
| 2016/0179250 A1* | 6/2016 | Nakajima | G06F 3/044 |
| | | | 345/174 |
| 2017/0315698 A1* | 11/2017 | Yoden | G06F 3/04812 |
| 2019/0114812 A1* | 4/2019 | Mullen | G06T 11/001 |
| 2019/0365350 A1* | 12/2019 | Chiang | A61B 8/461 |

* cited by examiner

METHOD AND SYSTEM FOR PRESENTING FUNCTION DATA ASSOCIATED WITH A USER INPUT DEVICE AT A MAIN DISPLAY IN RESPONSE TO A PRESENCE SIGNAL PROVIDED VIA THE USER INPUT DEVICE

FIELD

Certain embodiments relate to medical imaging, and particularly ultrasound imaging. More specifically, certain embodiments relate to a method and system for detecting a presence and/or a position of a user at a physical user input device of a medical imaging system and providing visual feedback at a main display identifying a functionality and/or value associated with the presence and/or position of the user at the physical user input device.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Ultrasound systems typically include an ultrasound scanner, a control panel, and a main display. The control panel may include user input devices such as a keyboard, trackball, buttons, rotary encoders, and/or a touch panel, among other things. An ultrasound operator may manually maneuver the ultrasound scanner on a patient while interacting with the user input devices on the control panel and viewing the ultrasound image data at the main display during an ultrasound examination. Accordingly, the ultrasound operator may have to repeatedly look away from the main display to locate the appropriate user input devices on the control panel to manipulate or adjust the functionality of the ultrasound system during the examination, which may be inefficient.

Ultrasound examinations are typically performed in low light conditions, which may make it difficult to identify an appropriate user input device to perform a desired functionality. In some cases, different models of ultrasound systems may have different physical configurations of the user input devices. Furthermore, the functionality of the user input devices may be different depending on the type of ultrasound examination being performed. Indeed, some ultrasound systems include user input devices that are programmable for a user-defined function, such as saving the image and transmitting the image to Digital Imaging and Communications in Medicine (DICOM) storage. Accordingly, an ultrasound operator may find it difficult to recall the functionality associated with each user input device for each ultrasound application.

In various applications, different rotary encoders may be used to rotate displayed image data about an X axis, Y axis, and/or Z axis. For example, one type of an ultrasound examination may present three orthogonal planes (e.g., an A plane, a B plane, and a C plane) at the main display. The ultrasound operator may turn a rotary encoder associated with the X axis to horizontally rotate the A plane and the C plane. The ultrasound operator may turn a rotary encoder associated with the Y axis to vertically rotate the A plane and the B plane. In some cases, a less experienced ultrasound operator may not readily recall the appropriate rotary encoder for manipulating the desired planes in the desired direction.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for detecting a presence and/or a position of a user at a physical user input device and providing visual feedback at a main display identifying a functionality and/or value associated with the presence and/or position of the user at the physical user input device, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
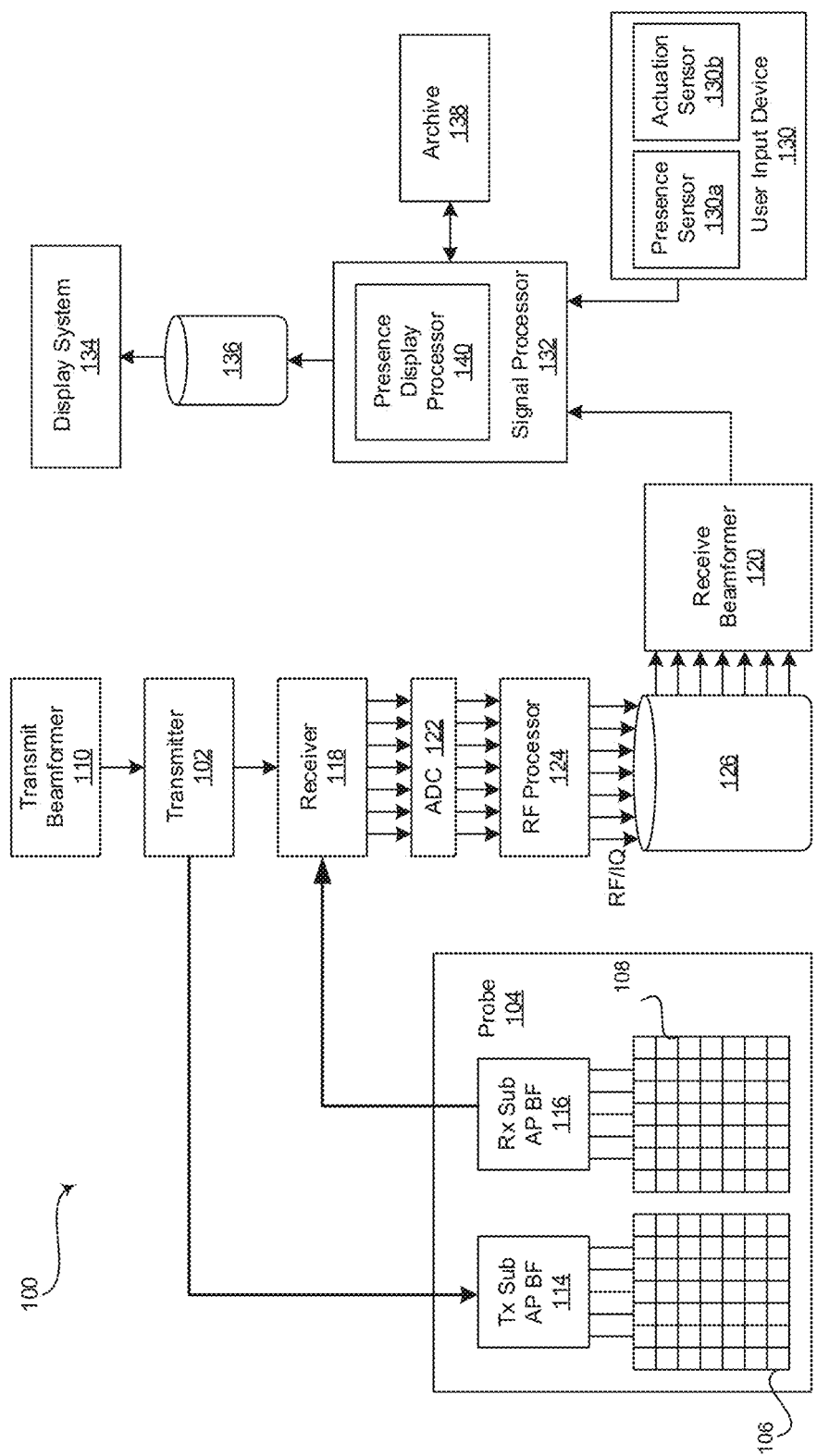
FIG. 1 is a block diagram of an exemplary ultrasound system that is operable to present function data associated with a user input device at a main display in response to a presence signal provided via the user input device, in accordance with various embodiments.

Certain embodiments may be found in a method and system for presenting function data associated with a user input device at a main display in response to a presence signal provided via the user input device. Various embodiments have the technical effect of providing visual feedback on a main display related to functionality of a user input device that is touching and/or in close proximity to an operator such that the operator does not have to look away from the main display. Certain embodiments have the technical effect of providing visual feedback on a main display related to a current value adjustable by a user input device that is touching and/or in close proximity to an operator. Various embodiments have the technical effect of overlaying, on a main display, a functionality and/or values associated with a selectable option on a touch panel in response to an operator touching or hovering over the selectable option on the touch panel such that the operator does not have to look away from the main display to navigate the touch panel.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments are described herein with reference to user input devices of an ultrasound system. For example, FIG. 1 illustrates an exemplary ultrasound system and FIGS. 2-6 illustrate an exemplary main display and control panel having user input devices of an ultrasound system. However, aspects of the present invention are not limited to ultrasound systems. Instead, any medical device having a main display and user input devices is contemplated.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to present function data associated with a user input device 130 at a main display 134 in response to a presence signal provided via the user input device 130, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system (also referred to as a main display) 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touch panel, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The user input device 130 may comprise a presence sensor 130a and an actuation sensor 130b. The actuation sensor 130b may comprise suitable logic, circuitry, interfaces and/or code that may be operable to detect the actuation of the user input device 130. For example, the actuation sensor 130b may detect the depression of a keyboard button, the rolling of a trackball, the depression of a button, the rotation of a rotary encoder, and the like. The presence sensor 130a may comprise suitable logic, circuitry, interfaces and/or code that may be operable to detect a presence of a user, such as a touch or close proximity of a user finger to the presence sensor 130a of the user input device 130. The detection of the presence of a user is separate from any subsequent or simultaneous detection of an actuation by the actuation sensor 130b. The presence sensor 130a may be a capacitive sensor, infrared sensor, or any suitable sensor operable to detect the presence of a user touching and/or in close proximity to the sensor. For example, the presence sensor 130a may be a capacitive touch/proximity switch having a remote sensing plate, such as conductive foil or the like, coupled to an integrated circuit. The remote sensing plate may be on, below, or integrated with an outer surface of the user input device 130. As an example, the remote sensing plate may be on, below, or integrated with a surface of a keyboard key, trackball, button, rotary encoder, or the like. The integrated circuit of the presence sensor 130a may be configured to receive a detection signal corresponding with a change in capacitance from the remote sensing plate. The integrated circuit may be configured to transmit a presence signal to the signal processor 132 of the ultrasound system 100 in response to the detection signal indicating a presence of a user at the user input device 130. In various embodiments, the sensitivity of the presence sensor 130a may be adjustable. For example, the presence sensor 130a sensitivity may be adjusted to detect a touch from a bare user finger (low sensitivity), a user finger wearing a glove (middle sensitivity), a user finger in close proximity of the presence sensor 130a (high sensitivity), or any suitable sensitivity.

In certain embodiments, the user input device 130 may be a touch panel having presence 130a and actuation 130b sensors and/or sensing functionality. For example, the presence 130a and actuation 130b sensing may be performed by resistive film touch panels, surface capacitive touch panels, projected capacitive touch panels, surface acoustic wave (SAW) touch panels, optical touch panels (e.g., infrared optical imaging touch panels), electromagnetic induction touch panels, or any suitable touch panel. In various embodiments, the touch panel user input device 130 may be configured in a number of ways to distinguish between presence and actuation. For example, presence may be detected by a light touch or hovering over a location of the touch panel and actuation may be detected by a firm touch at a location of the touch panel. As another example, presence may be detected by a touch input at a location of the touch panel and actuation may be detected by a double touch at a location of the touch panel. Another example may include a single finger at a location of the touch panel corresponding with a presence detection and a multi-touch input (e.g., two fingers) may correspond with a detected actuation. As another example, presence may be detected by a touch input at a location of the touch panel for less than a predetermined amount of time and actuation may be defined by a touch input at a location of the touch panel for more than the predetermined amount of time. In various embodiments, the touch panel may be configurable to define presence sensing functionality and actuation sensing functionality.

The signal processor 132 may comprise suitable logic, circuitry, interfaces and/or code that may be operable to process ultrasound scan data (i.e., summed IQ signal) for generating ultrasound images for presentation on a display system (also referred to as a main display) 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a presence display processor 140 and may be capable of receiving input information from user input devices 130 and/or archive 138, generating an output displayable by a display system 134, and manipulating the output in response to input information from a user input device 130, among other things. The signal processor 132 and presence display processor 140 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a presence display processor 140 that comprises suitable logic, circuitry, interfaces and/or code that may be operable to receive a presence signal from a presence sensor 130a of a user input device 130 and to present function data corresponding with the functionality of the user input device 130 at the display system 134 in response to the received presence signal. The function data may be highlighting, marking, overlaid text or values, or any suitable mechanism for drawing attention to a functionality and/or the current setting value associated with a functionality. For example, the function data may be highlighted or marked displayed function text, values and/or icons. As another example, the function data may be text and/or values describing a functionality and/or the current value associated with the functionality that is superimposed on the display system 134.

The presence display processor 140 may access information associating one or more user input devices 130 with a functionality and/or the current setting value of a functionality. The association information may be accessed based on a selected imaging mode and/or imaging application. For example, a programmable button user input device 130 may be associated with a user selected functionality, such as print an image, store an image, send an image to DICOM storage, and/or any suitable functionality or combinations of functionalities for one or more modes and/or applications. Other button user input devices 130 may have pre-defined functionality, such as specifying a particular imaging mode, entering a measurement mode, or any suitable pre-defined functionality. Rotary encoder user input devices 130 may be associated with image setting value adjustments (e.g., brightness, contrast, etc.), image rotation functionality (e.g., rotating one or more images about an X-axis, Y-axis, or Z-axis), or any suitable functionality for one or more modes and/or applications. In various embodiments, a functionality corresponding with one or more of the user input devices 130 may be presented at the display system 134. For example, a print icon, save icon, different mode text or icons (e.g., measurement mode, change light source mode, etc.), arrows corresponding with image rotation directions, and the like may be visible at the display system 134 continuously or at appropriate times (e.g., when the functionality is available).

The presence display processor 140 may be configured to highlight, mark, or otherwise provide a visual indicator (i.e., function data) identifying an icon, text, value, arrow, or the like at the display system 134 corresponding with a user input device 130 in response to receiving a presence signal from the presence sensor 130a of that user input device 130 so that a user does not need to look away from the display system 134 to locate an appropriate user input device 130. For example, a user may move a finger over different user input devices 130 on a control panel of an ultrasound system 100 and corresponding functionality will be identified by function data so that a user is aware of the functionality corresponding with user input device 130 that the finger of the user is touching or hovering over. The user may actuate the appropriate user input device 130 once located and the actuation sensor 130b of the user input device 130 provides an actuation signal to the signal processor 132 for selecting or adjusting the associated functionality.

In various embodiments, the presence display processor 140 may be configured to overlay text and/or a current setting value associated with a functionality in response to a received presence signal. For example, a touch panel user input device 130 may send a presence signal corresponding with a location on the touch panel user input device 130 that a user finger is touching or hovering over. The presence display processor 140 may superimpose text and/or a current setting value on the display system 134 corresponding to the location on the touch panel so that the user may select or adjust the functionality identified on the touch panel and overlaid on the display system 134 without having to look at the touch panel user input device 130.

FIGS. 2-6 are displays of an exemplary main display 400 and control panel 200 having user input devices 210-250, the main display 400 configured to present function data 430 associated with a user input device in response to a presence signal provided via the user input device, in accordance with various embodiments. The main display 400 of FIGS. 2-6 may be the display system 134 of FIG. 1 The user input devices 210-250 of FIGS. 2-6 may be the user input device 130 of FIG. 1. Referring to FIGS. 2-6, there is shown a control panel 200 and a main display 400. The control panel 200 comprises user input devices including a keyboard 210, trackball 220, buttons 230 surrounding the trackball 220, other standalone buttons 240, rotary encoders 250, and a touch panel 300. The user input devices 210-250,300 may include a presence sensor and actuation sensor. The touch panel 300 shown in FIG. 6 includes selectable functionality 310 and adjustable settings values functionality 320. The main display 400 of FIGS. 2-6 comprises ultrasound images 410, selectable and/or adjustable functionality 420, and function data 430.

Figure 2:
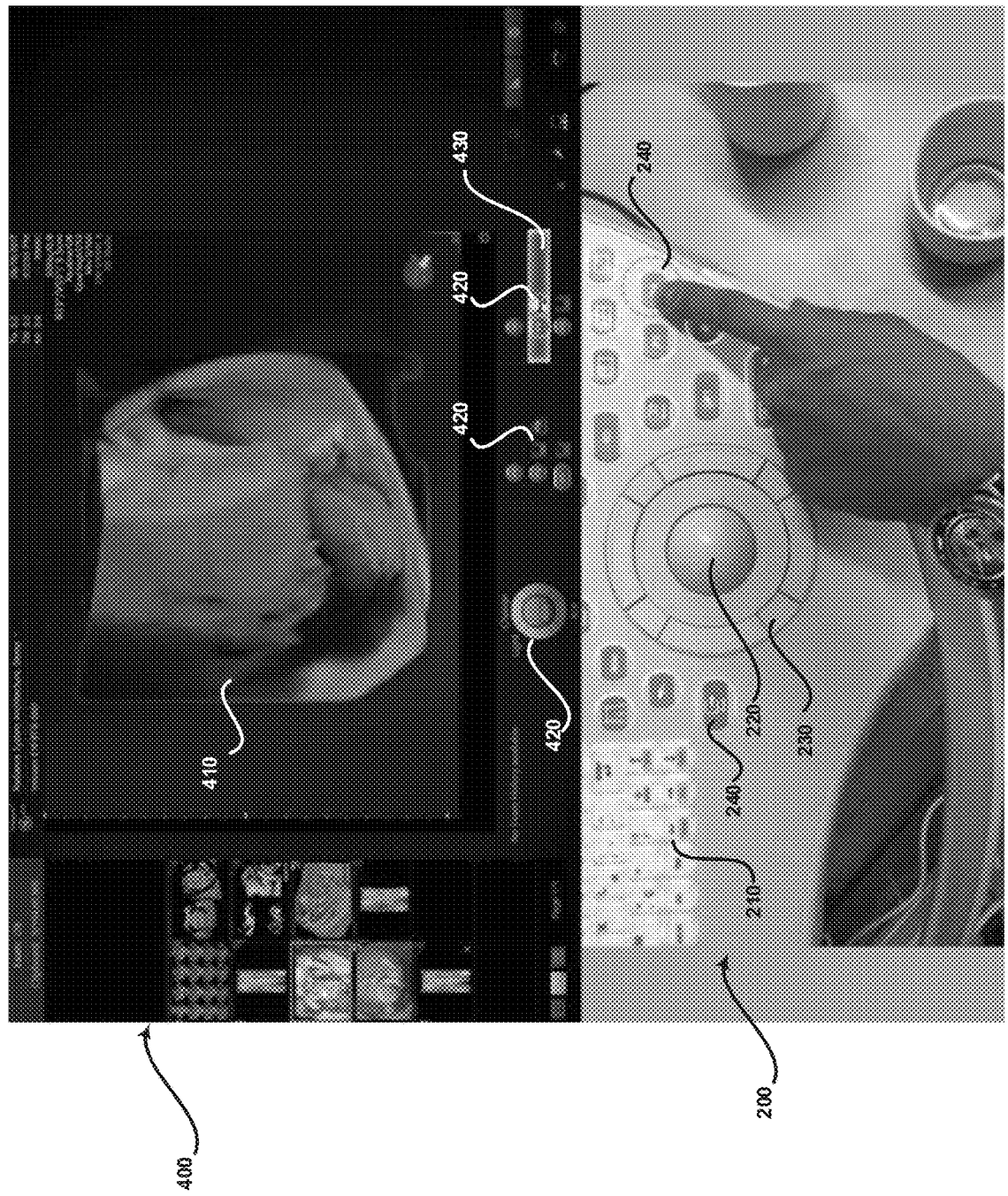
FIG. 2 is a display of an exemplary main display and control panel having user input devices, the main display configured to present function data associated with a user input device in response to a presence signal provided via the user input device, in accordance with various embodiments.
Figure 3:
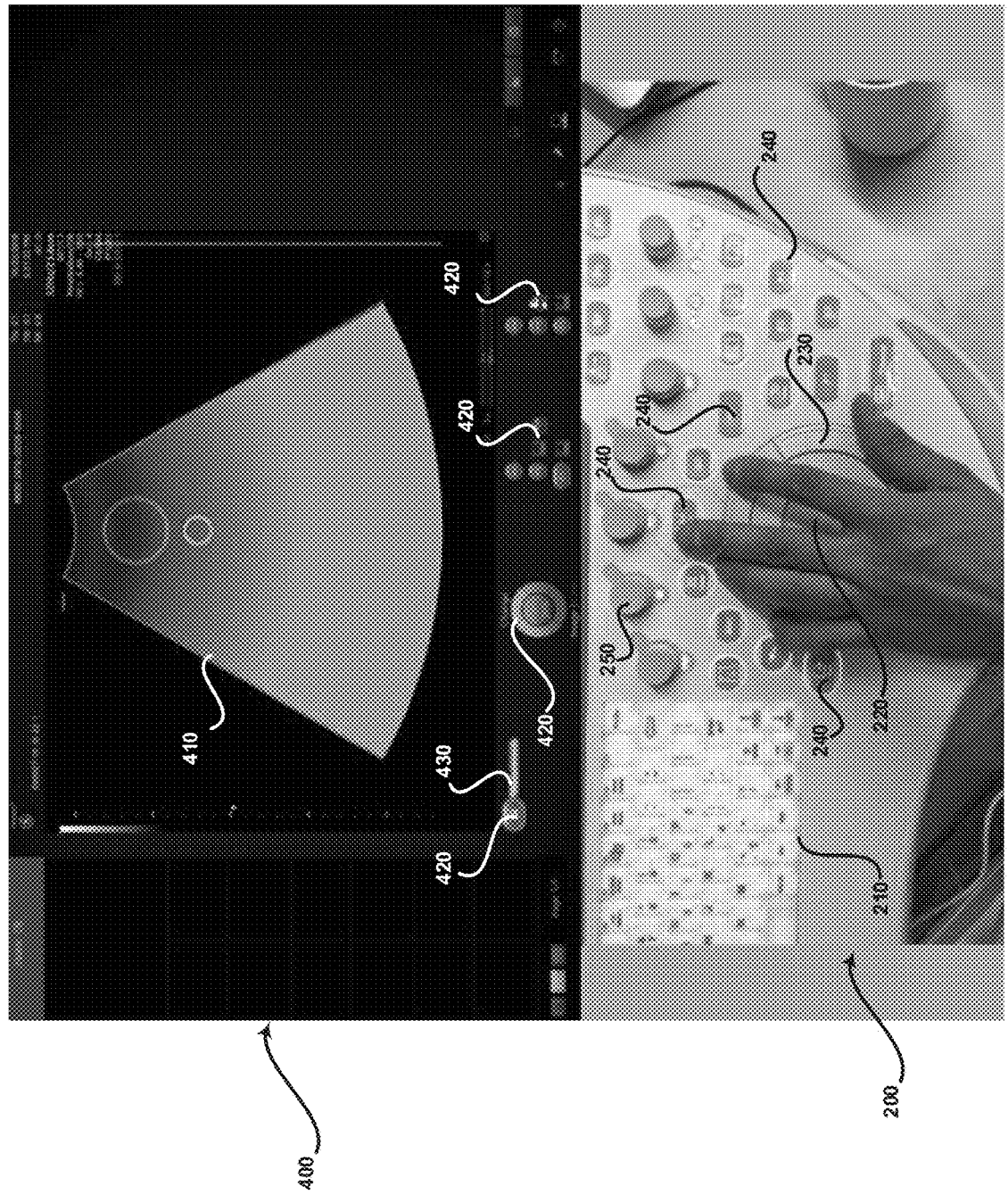
FIG. 3 is a display of an exemplary main display and control panel having user input devices, the main display configured to present function data associated with a user input device in response to a presence signal provided via the user input device, in accordance with various embodiments.
Figure 4:
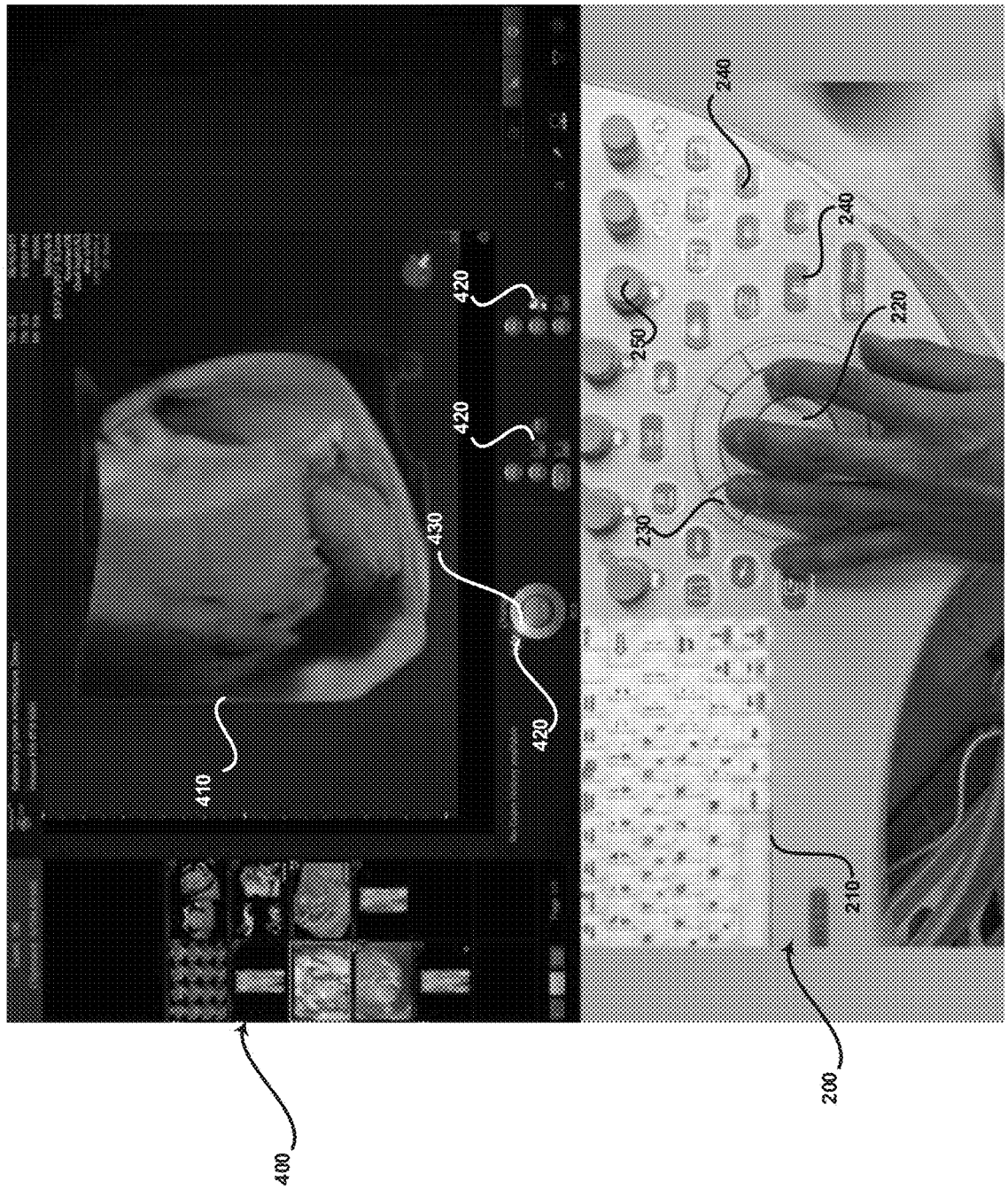
FIG. 4 is a display of an exemplary main display and control panel having user input devices, the main display configured to present function data associated with a user input device in response to a presence signal provided via the user input device, in accordance with various embodiments.
Figure 5:
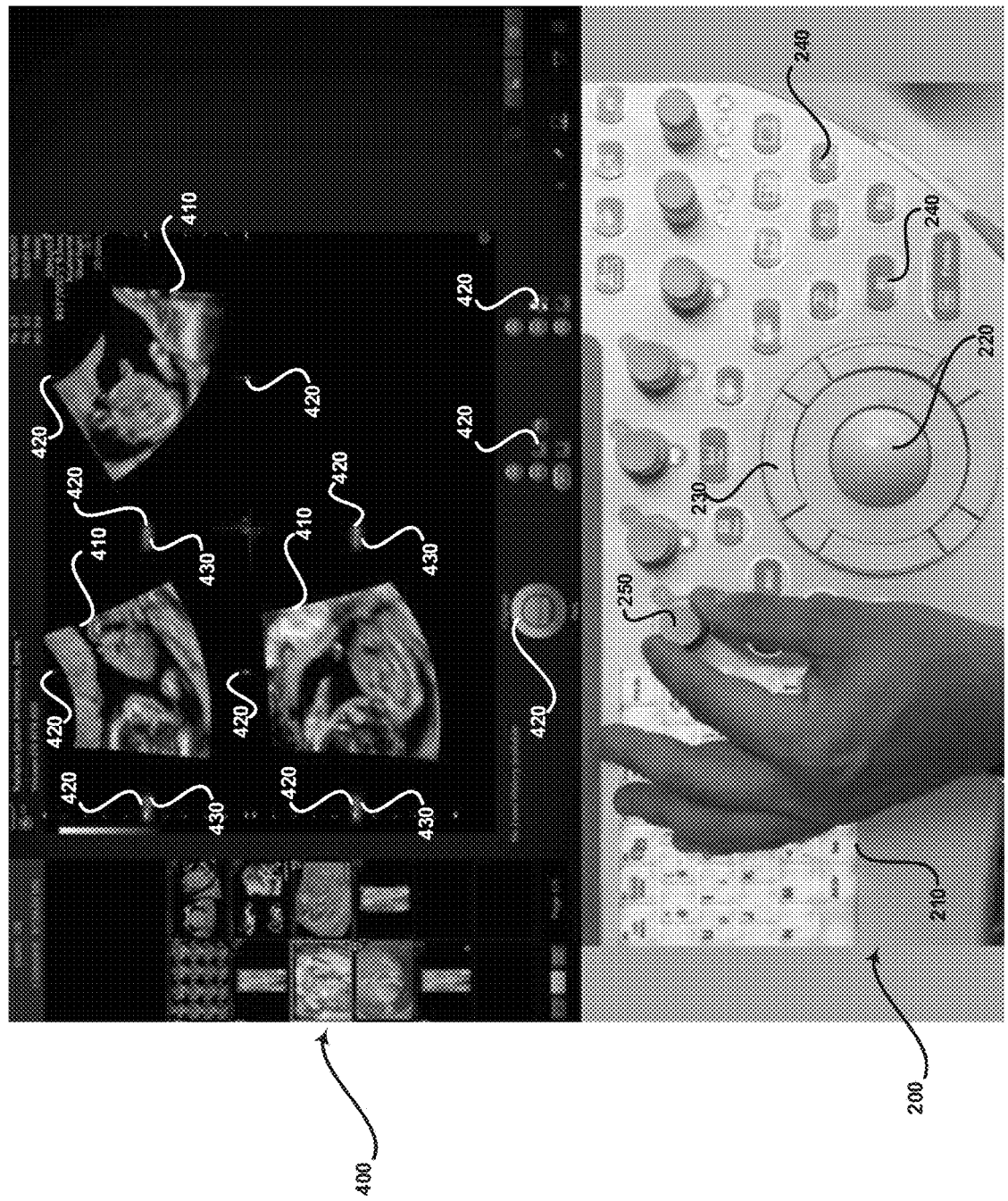
FIG. 5 is a display of an exemplary main display and control panel having user input devices, the main display configured to present function data associated with a user input device in response to a presence signal provided via the user input device, in accordance with various embodiments.
Figure 6:
FIG. 6 is a display of an exemplary main display and control panel having user input devices, the main display configured to present function data associated with a user input device in response to a presence signal provided via the user input device, in accordance with various embodiments.

Referring to FIG. 2, function data 430 highlighting a print function 420 is presented at the main display 400 in response to a user hovering over or touching a button 240 corresponding with the highlighted print function 420. Referring to FIG. 3, function data 430 highlighting a measurements mode function 420 is presented at the main display 400 in response to a user hovering over or touching a button 240 corresponding with the highlighted measurement mode function 420. Referring to FIGS. 4 and 6, function data 430 highlighting a change light source mode function 420 is presented at the main display 400 in response to a user hovering over or touching a button 230 adjacent the trackball 220 that corresponds with the highlighted change light source mode function 420. Referring to FIG. 5, function data 430 highlighting horizontal arrows 420 adjacent an A-plane ultrasound image 410 and a C-plane ultrasound image 410 is presented at the main display 400 in response to a user grasping a rotary encoder 250 for rotating ultrasound image data 410 about an X-axis. The highlighted 430 horizontal arrows 420 identify both the ultrasound images 410 and the rotation direction corresponding with the rotary encoder 250 grasped by the user.

Referring to FIG. 6, a touch panel user input device 300 is provided on the control panel 200 with the other user input devices 210-250. In various embodiments, a textual description is superimposed on the main display 400 in response to a user touching or hovering over a selectable functionality 310 on the touch panel 300. In certain embodiments, a textual description and/or current setting value is superimposed on the main display in response to a user touching or hovering over a selectable and/or adjustable functionality 320 or in response to a user touching or in close proximity to a user input device corresponding with the selectable and/or adjustable functionality 320, such as an adjacent rotary encoder 250 as illustrated in FIG. 6. The setting value superimposed on the main display 400 may dynamically update in response to actuation of the user input device, such as by rotating the rotary encoder 250 corresponding with an image brightness or image contrast adjustable functionality 320 presented in the touch panel user input device 300.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present a main display 400 of information from the signal processor 132 and/or archive 138, such as ultrasound image data 410, functionality 420 represented by text, icon, arrows, or the like, function data 430 such as highlighting, marking, superimposed text, superimposed setting values, and the like, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores associations between image acquisition, processing, display, storage, transmission, and/or printing functionality and corresponding user input devices 130 for carrying out the associated functionality, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms.

Figure 7:
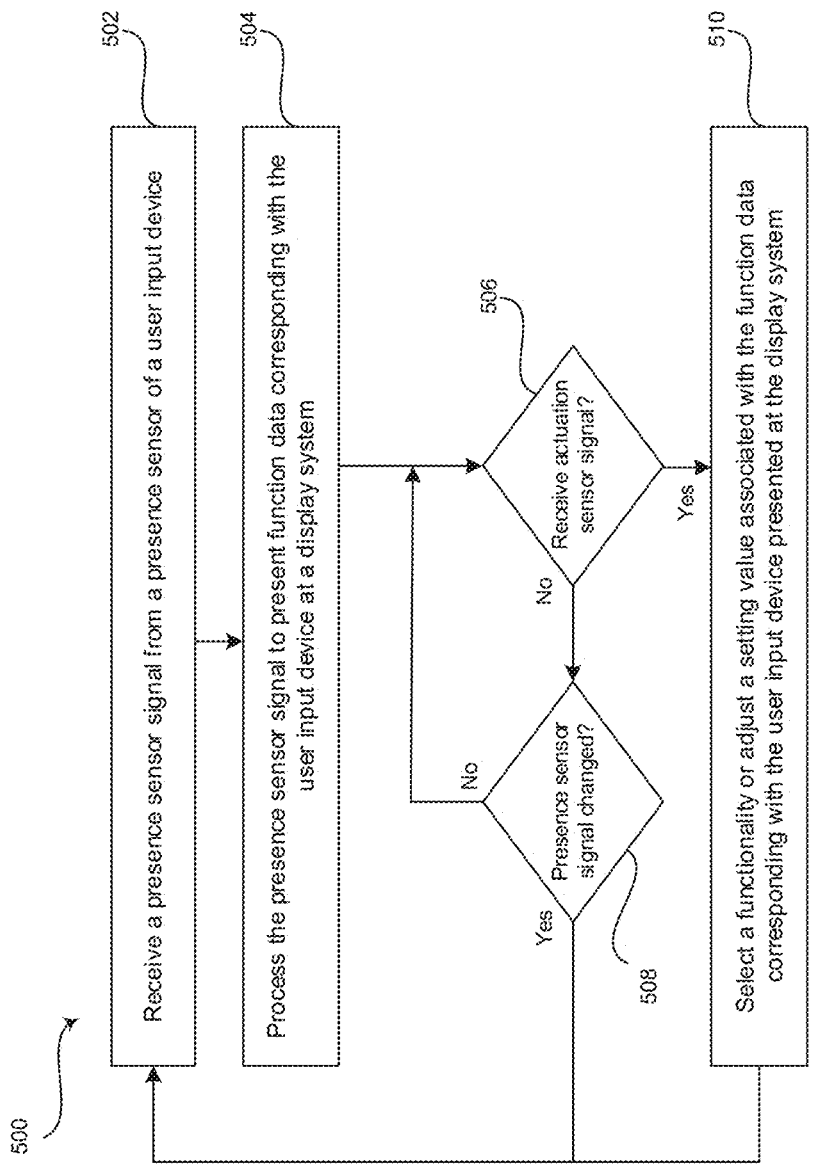
FIG. 7 is a flow chart illustrating exemplary steps that may be utilized for presenting function data associated with a user input device at a main display in response to a presence signal provided via the user input device, in accordance with various embodiments.

FIG. 7 is a flow chart 500 illustrating exemplary steps 502-510 that may be utilized for presenting function data 430 associated with a user input device 210-250 at a main display 134, 400 in response to a presence signal provided via the user input device 210-250, in accordance with various embodiments. Referring to FIG. 7, there is shown a flow chart 500 comprising exemplary steps 502 through 510. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, a signal processor 132 of an ultrasound system 100 may receive a presence signal from a presence sensor 130a of a user input device 130. For example, the user input device 130 may be a button 230, 240, rotary encoder 250, touch panel 300, trackball 220, keyboard 210, or the like. The user input device 130 may include a presence sensor 130a and an actuation sensor 130b. The presence sensor 130a may be operable to detect the presence of a user touching and/or hovering over the user input device 130. The presence sensor 130a may be a capacitive sensor, infrared sensor, or any suitable sensor. The presence sensor 130a may be operable to send a presence signal to a presence display processor 140 in response to detection of the user touching and/or hovering over the user input device 130. The actuation sensor 130b may be operable to detect an actuation of the user input device 130. For example, the actuation sensor 130b may provide the signal processor 132 with an actuation signal corresponding with the depression of a button, rotation of a rotary encoder, rolling of a trackball, selection of touch panel option, or any suitable user input device 130 actuation.

At step 504, the signal processor 132 of the ultrasound system 100 may process the presence signal to present function data 430 corresponding with the user input device 130 at a display system 134. For example, a presence display processor 140 of the signal processor 132 may process the presence signal received from the presence sensor 130a of the user input device 130 at step 502. The presence display processor 140 may identify the user input device 130 that provided the presence signal and identify the functionality associated with that user input device 130. The presence display processor 140 may display function data 430 to identify the functionality 420 of the user input device 130 at a main display 400 of the display system 134. The function data 430 may be highlighting or marking of a displayed functionality 420 of the user input device 130, text or a setting value of the functionality 420 of the user input device 130, or any suitable information identifying the functionality 420 of the user input device 130. The function data 430 presented by the presence display processor 140 may allow a user to determine if the user is touching or hovering over a user input device 130 associated with a desired functionality 420 so that the user does not need to look away from the main display 400 of the display system.

At step 506, the signal processor 132 of the ultrasound system 100 may determine whether an actuation signal has been received. For example, the signal processor 132 may determine whether an actuation signal was received from the actuation sensor 130*b* of the user input device 130. The actuation signal may correspond with the function data 430 identifying the functionality 420 of the user input device 130 that is presented at the main display 400 of the display system 134. If the signal processor 132 received an actuation signal from the actuation sensor 130*b* of the user input device 130, the process proceeds to step 510. If the signal processor 132 has not received an actuation signal from the actuation sensor 130*b* of the user input device 130, the process proceeds to step 508.

At step 508, the signal processor 132 of the ultrasound system 100 may determine whether the presence signal has changed. For example, the presence display processor 140 may actively monitor the presence signal received from the presence sensor 130*a* of the user input device 130 to determine whether a user is still hovering over and/or touching the user input device 130. If the presence signal has not changed, indicating that the presence sensor 130*a* is still detecting a user in a defined proximity of the user input device 130, steps 506 and 508 may be repeated until the signal processor receives an actuation signal at step 506 or the presence display processor 140 detects a change in the presence signal at step 508. If the presence signal has changed (e.g., the presence sensor 130*a* is no longer detecting a user presence and/or a presence signal is received from a different presence sensor 130*a* of a different user input device 130), the process may proceed to step 502 when a different presence signal is received.

At step 510, the signal processor 132 of the ultrasound system 100 may select a functionality 310, 420 or adjust a value 320 associated with the function data 430 corresponding with the user input device 130 presented at the main display 400 of the display system 134. For example, the signal processor 132 may select the functionality 310, 420 highlighted, marked, or otherwise identified 430 by the function data in response to receiving the actuation signal from the actuation sensor 130*b* of the user input device 130 at step 506. As an example, if a user was touching or hovering over a user input device 130 associated with a measurement mode, the measurement mode functionality 420 may be highlighted or otherwise presented 430 on the main display 400 of the display system 134 at step 504. If the user actuates the user input device 130 at step 506, the signal processor 132 may select the measurement mode functionality 420 to enter the measurement mode at step 510. The process may return to step 502 when the presence display processor 140 receives a new presence signal from a presence sensor 130*a* of a user input device 130.

Aspects of the present disclosure provide a method 500 and system 100 for presenting function data 430 associated with a user input device 130, 210-250, 300 at a main display 134, 400 in response to a presence signal provided via the user input device 130, 210-250, 300. In accordance with various embodiments, the method 500 may comprise receiving 502, at a processor 132, 140 of an ultrasound system 100, a presence signal from a presence sensor 130*a* of a user input device 130, 210-250, 300 of the ultrasound system 100. The presence signal is provided by the presence sensor 130*a* in response to a detection of a user at a proximity to the user input device 130, 210-250, 300. The presence signal is independent from an actuation signal provided by the user input device 130, 210-250, 300 in response to user actuation of the user input device 130, 210-250, 300. The method 500 may comprise processing 504, by the processor 132, 140, the presence signal to present function data 430 identifying a functionality 420 of the user input device 130, 210-250, 300 at a main display 134, 400 of the ultrasound system 100.

In a representative embodiment, the method 500 may comprise receiving 506, by the processor 132, 140, the actuation signal from the user input device 130, 210-250, 300 in response to the user actuation of the user input device 130, 210-250, 300. The method 500 may comprise one or both of selecting 510, by the processor 132, 140, the functionality 420 of the user input device 130, 210-250, 300 identified by the function data 430 presented at the main display 134, 400 or adjusting 510, by the processor 132, 140, a setting value associated with the functionality 420 of the user input device 130, 210-250, 300 identified by the function data 430 presented at the main display 134, 400. In an exemplary embodiment, the proximity of the user to the user input device 130, 210-250, 300 is one or both of the user hovering over the user input device 130, 210-250, 300, or the user touching the user input device 130, 210-250, 300. In various embodiments, the user input device 130, 210-250, 300 is one of a button 230, 240, a rotary encoder 250, or a touch panel 300.

In certain embodiments, the presence sensor 130*a* is a capacitive sensor. In a representative embodiment, the capacitive sensor is adjustable to define the proximity of the user to the user input device 130, 210-250, 300 for detection. In various embodiments, the function data 430 is a highlighting or marking identifying one or more of a displayed functionality 420 icon, at least one arrow, text, and setting value. In an exemplary embodiment, the function data 430 is superimposed on the main display 134, 400, the function data 430 being one or both of text and a setting value.

Various embodiments provide an ultrasound system 100 for presenting function data 430 associated with a user input device 130, 210-250, 300 at a main display 134, 400 in response to a presence signal provided via the user input device 130, 210-250, 300. The ultrasound system 100 may comprise a user input device 130, 210-250, 300, at least one processor 132, 140, and a main display 134, 400. The user input device 130, 210-250, 300 may comprise a presence sensor 130*a*. The user input device 130, 210-250, 300 may be operable to provide a presence signal in response to a detection of a user at a proximity to the user input device 130, 210-250, 300 by the presence sensor 130*a*. The user input device 130, 210-250, 300 may be operable to provide an actuation signal, independent from the presence signal, in response to a user actuation of the user input device 130, 210-250, 300. The at least one processor 132, 140 may be configured to receive the presence signal from the presence sensor 130a of the user input device 130, 210-250, 300. The at least one processor 132, 140 may be configured to process the presence signal to present function data 430 identifying a functionality 420 of the user input device 130, 210-250, 300. The main display 134, 400 may be operable to present the function data 430 identifying the functionality 420 of the user input device 130, 210-250, 300.

In an exemplary embodiment, the at least one processor 132, 140 may be configured to receive the actuation signal from the user input device 130, 210-250, 300 in response to the user actuation of the user input device 130, 210-250, 300. The at least one processor 132, 140 may be configured to one or both of select the functionality 420 of the user input device 130, 210-250, 300 identified by the function data 430 presented at the main display 134, 400 or adjust a setting value associated with the functionality 420 of the user input device 130, 210-250, 300 identified by the function data 430 presented at the main display 134, 400. In certain embodiments, the proximity of the user to the user input device 130, 210-250, 300 may be one or both of the user hovering over the user input device 130, 210-250, 300 or the user touching the user input device 130, 210-250, 300.

In various embodiments, the user input device 130, 210-250, 300 may be one of a button 230, 240, a rotary encoder 250, or a touch panel 300. In a representative embodiment, the presence sensor 130a may be a capacitive sensor. The capacitive sensor may be adjustable to define the proximity of the user to the user input device 130, 210-250, 300 for detection. In an exemplary embodiment, the function data 430 may be a highlighting or marking identifying one or more of a displayed functionality 420 icon, at least one arrow, text, and setting value. In various embodiments, the at least one processor 132, 140 is configured to superimpose the function data 430 on the main display 134, 400. The function data 430 may be one or both of text and a setting value.

Certain embodiments provide a non-transitory computer readable medium having stored thereon, a computer program having at least one code section. The at least one code section is executable by a machine for causing the machine to perform steps 500. The steps 500 may comprise receiving 502 a presence signal from a presence sensor 130a of a user input device 130, 210-250, 300 of an ultrasound system 100. The presence signal may be provided by the presence sensor 130a in response to a detection of a user at a proximity to the user input device 130, 210-250, 300. The presence signal may be independent from an actuation signal provided by the user input device 130, 210-250, 300 in response to user actuation of the user input device 130, 210-250, 300. The steps 500 may comprise processing 504 the presence signal to present function data 430 identifying a functionality 420 of the user input device 130, 210-250, 300 at a main display 134, 400 of the ultrasound system 100.

In a representative embodiment, the steps 500 may comprise receiving 506 the actuation signal from the user input device 130, 210-250, 300 in response to the user actuation of the user input device 130, 210-250, 300. The steps 500 may comprise one or both of selecting 510 the functionality 420 of the user input device 130, 210-250, 300 identified by the function data 430 presented at the main display 134, 400 or adjusting 510 a setting value associated with the functionality 420 of the user input device 130, 210-250, 300 identified by the function data 430 presented at the main display 134, 400. In an exemplary embodiment, the proximity of the user to the user input device 130, 210-250, 300 may be one or both of the user hovering over the user input device 130, 210-250, 300 or the user touching the user input device 130, 210-250, 300. In various embodiments, the function data 430 may be a highlighting or marking identifying one or more of a displayed functionality 420 icon, at least one arrow, text, and setting value. In certain embodiments, the function data 430 may be superimposed on the main display 134, 400. The function data 430 may be one or both of text and a setting value.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for presenting function data associated with a user input device at a main display in response to a presence signal provided via the user input device.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   receiving, at a processor of an ultrasound system, a presence signal from a presence sensor of a user input device of the ultrasound system, wherein the presence signal is provided by the presence sensor in response to a detection of a user at a proximity to the user input device, and wherein the presence signal is independent from an actuation signal provided by the user input device in response to user actuation of the user input device; and
   processing, by the processor, the presence signal to present function data identifying a functionality of the user input device at a main display of the ultrasound system.

2. The method of claim 1, comprising:
   receiving, by the processor, the actuation signal from the user input device in response to the user actuation of the user input device; and
   one or both of:
      selecting, by the processor, the functionality of the user input device identified by the function data presented at the main display, or
      adjusting, by the processor, a setting value associated with the functionality of the user input device identified by the function data presented at the main display.

3. The method of claim 1, wherein the proximity of the user to the user input device is one or both of:
   the user hovering over the user input device, or
   the user touching the user input device.

4. The method of claim 1, wherein the user input device is one of:
   a button,
   a rotary encoder, or
   a touch panel.

5. The method of claim 1, wherein the presence sensor is a capacitive sensor.

6. The method of claim 5, wherein the capacitive sensor is adjustable to define the proximity of the user to the user input device for detection.

7. The method of claim 1, wherein the function data is a highlighting or marking identifying one or more of a displayed functionality:
   icon,
   at least one arrow,
   text, and
   setting value.

8. The method of claim 1, wherein the function data is superimposed on the main display, the function data being one or both of text and a setting value.

9. An ultrasound system comprising:
   a user input device comprising a presence sensor, the user input device operable to:
      provide a presence signal in response to a detection of a user at a proximity to the user input device by the presence sensor, and
      provide an actuation signal, independent from the presence signal, in response to a user actuation of the user input device;
   at least one processor configured to:
      receive the presence signal from the presence sensor of the user input device, and
      process the presence signal to present function data identifying a functionality of the user input device; and
   a main display operable to present the function data identifying the functionality of the user input device.

10. The ultrasound system of claim 9, wherein the at least one processor is configured to:
    receive the actuation signal from the user input device in response to the user actuation of the user input device; and
    one or both of:
       select the functionality of the user input device identified by the function data presented at the main display, or
       adjust a setting value associated with the functionality of the user input device identified by the function data presented at the main display.

11. The ultrasound system of claim 9, wherein the proximity of the user to the user input device is one or both of:
    the user hovering over the user input device, or
    the user touching the user input device.

12. The ultrasound system of claim 9, wherein the user input device is one of:
    a button,
    a rotary encoder, or
    a touch panel.

13. The ultrasound system of claim 9, wherein the presence sensor is a capacitive sensor, the capacitive sensor adjustable to define the proximity of the user to the user input device for detection.

14. The ultrasound system of claim 9, wherein the function data is a highlighting or marking identifying one or more of a displayed functionality:
    icon,
    at least one arrow,
    text, and
    setting value.

15. The ultrasound system of claim 9, wherein the at least one processor is configured to superimpose the function data on the main display, the function data being one or both of text and a setting value.

16. A non-transitory computer readable medium having stored thereon, a computer program having at least one code section, the at least one code section being executable by a machine for causing the machine to perform steps comprising:
    receiving a presence signal from a presence sensor of a user input device of an ultrasound system, wherein the presence signal is provided by the presence sensor in response to a detection of a user at a proximity to the user input device, and wherein the presence signal is independent from an actuation signal provided by the user input device in response to user actuation of the user input device; and
    processing the presence signal to present function data identifying a functionality of the user input device at a main display of the ultrasound system.

17. The non-transitory computer readable medium of claim 16, comprising:
    receiving the actuation signal from the user input device in response to the user actuation of the user input device; and
    one or both of:
       selecting the functionality of the user input device identified by the function data presented at the main display, or adjusting a setting value associated with the functionality of the user input device identified by the function data presented at the main display.

18. The non-transitory computer readable medium of claim 16, wherein the proximity of the user to the user input device is one or both of:
the user hovering over the user input device, or
the user touching the user input device.

19. The non-transitory computer readable medium of claim 16, wherein the function data is a highlighting or marking identifying one or more of a displayed functionality:
icon,
at least one arrow,
text, and
setting value.

20. The non-transitory computer readable medium of claim 16, wherein the function data is superimposed on the main display, the function data being one or both of text and a setting value.

* * * * *